(12) United States Patent
Seppa et al.

(10) Patent No.: US 10,034,620 B2
(45) Date of Patent: Jul. 31, 2018

(54) MEASURING LUNG VOLUME CHANGES BY IMPEDANCE PNEUMOGRAPHY

(71) Applicant: TAMPEREEN TEKNILLINEN YLIOPISTO, Tampere (FI)

(72) Inventors: Ville-Pekka Seppa, Tampere (FI); Jari Viik, Tampere (FI)

(73) Assignee: TIDE MEDICAL OY, Tampere (FI)

( * ) Notice: Subject to any disclaimer, the term of this patent is extended or adjusted under 35 U.S.C. 154(b) by 745 days.

(21) Appl. No.: 14/390,229

(22) PCT Filed: Apr. 3, 2013

(86) PCT No.: PCT/FI2013/050361
§ 371 (c)(1),
(2) Date: Oct. 2, 2014

(87) PCT Pub. No.: WO2013/150185
PCT Pub. Date: Oct. 10, 2013

(65) Prior Publication Data
US 2015/0051469 A1 Feb. 19, 2015

(30) Foreign Application Priority Data
Apr. 3, 2012 (FI) .................................. 20125376

(51) Int. Cl.
*A61B 5/08* (2006.01)
*A61B 5/091* (2006.01)
(Continued)

(52) U.S. Cl.
CPC .......... *A61B 5/0809* (2013.01); *A61B 5/0004* (2013.01); *A61B 5/0535* (2013.01);
(Continued)

(58) Field of Classification Search
CPC ... A61B 5/0004; A61B 5/0535; A61B 5/0809; A61B 5/091; A61B 5/6825; A61B 5/72
See application file for complete search history.

(56) References Cited

U.S. PATENT DOCUMENTS 3,730,173 A * 5/1973 Deaton .................... A61B 5/02
340/573.1
2005/0141444 A1 8/2005 Ono et al.
(Continued)

FOREIGN PATENT DOCUMENTS

WO 9720499 6/1997
WO 2012104490 8/2012

OTHER PUBLICATIONS

Extended European Search Report for European Application No. EP 13773037.0, Completed by the European Patent Office, dated Nov. 17, 2015, 9 pages.
(Continued)

*Primary Examiner* — Eunhwa Kim
(74) *Attorney, Agent, or Firm* — Brooks Kushman P.C.

(57) ABSTRACT

A method, a sensor arrangement, an apparatus and a computer program product for measuring a change in lung volume, having measuring a parameter for impedance pneumography by using at least one electrode configured to be in contact with an arm of a human body and at least one electrode configured to be in skin contact with thorax of a human body.

4 Claims, 4 Drawing Sheets

(51) Int. Cl.
*A61B 5/00* (2006.01)
*A61B 5/053* (2006.01)

(52) U.S. Cl.
CPC ............ *A61B 5/091* (2013.01); *A61B 5/6805* (2013.01); *A61B 5/6825* (2013.01); *A61B 5/72* (2013.01)

(56) References Cited

U.S. PATENT DOCUMENTS

| | | | |
|---|---|---|---|
| 2006/0220883 A1 | 10/2006 | Matos | |
| 2007/0083096 A1* | 4/2007 | Paradiso | A61B 5/0408 600/388 |
| 2008/0009757 A1* | 1/2008 | Tsoglin | A61B 5/0535 600/506 |
| 2011/0087300 A1 | 4/2011 | Van Den Erenbeemd et al. | |
| 2011/0190647 A1 | 8/2011 | Helfenbein et al. | |
| 2011/0257489 A1* | 10/2011 | Banet | A61B 5/0809 600/301 |
| 2012/0041279 A1* | 2/2012 | Freeman | A61B 5/0205 600/301 |

OTHER PUBLICATIONS

International Search Report for PCT/FI2013/050361, Completed by the Finish Patent Office dated Jun. 28, 2013, 4 Pages.

Goldensohn et al. Department of Neurology, College of Physicians and Surgeons, Columbia University, and the Neurological Institute, Presbyterian Hospital 1958, p. 463-464, "An Electrical Impedance Spirometer."

Weltman et al. Journal of Applied Physiology Dec. 1969, vol. 27, No. 6, p. 907-909, "Impedance Pneumograph Recording Across the Arms."

Ansari et al. IEEE International Conference on Bioinformatics and Biomedicine Workshops 2011, p. 540-547, "Reduction of Periodic Motion Artifacts From Impedance Plethysmography."

Ansari et al. IEEE International Conference on Bioinformatics and Biomedicine 2009, p. 197-202, "Extraction of Respiratory Rate from Impedance Signal Measured on Arm: A Portable Respiratory Rate Measurement Device."

Baker., IEEE Engineering in Medicine and Biology Magazine Mar. 1989, p. 50-52, "Applications of the Impedance Technique to the Respiratory System."

Volk et al. 4th International Conference on Biomedical Engineering and Informatics (BMEI) 2011, p. 565-568, "Ventilation Distribution on Different Body Positions Measured by Electrical Impedance Tomography."

Zifan et al. IEEE International Conference on Imaging Systems and Techniques 2012, p. 57-62, "Fast and Robust Automated Segmentation of EIT Lung Images using an Anatomically Constrained Kalman Filter."

Seppa., Tampere University of Technology, Department of Electrical Engineering Master of Science Thesis Aug. 2007, 66 Pages, "Bioimpedance in a Wireless Wearable Device."

\* cited by examiner

MEASURING LUNG VOLUME CHANGES BY IMPEDANCE PNEUMOGRAPHY

CROSS-REFERENCE TO RELATED APPLICATION

This application is the U.S. national phase of PCT Application No. PCT/FI2013/050361 filed on Apr. 3, 2013, which claims priority to FI Patent Application No. 20125376 filed on Apr. 3, 2012, the disclosures of which are incorporated in their entirety by reference herein.

FIELD OF THE INVENTION

The invention relates to non-invasive lung volume measurement by impedance pneumography. More specifically, the invention relates to a method, a sensor arrangement, an apparatus and a computer program product for measuring a change in lung volume.

BACKGROUND OF THE INVENTION

Impedance pneumography (IP) provides a minimally intrusive mode of measurement for lung volume changes. In the IP recording a small high frequency current is passed through a pair of skin electrodes and another pair of electrodes is used to record the generated voltage that is proportional to the impedance (Z), which again is proportional to the lung volume (V). The current feeding and voltage measurement may also be combined into a single pair of electrodes.

Several studies have shown a linear relation between the thoracic impedance and the lung volume ($\Delta Z/\Delta V$) enabling an even pulmonary flow rate signal derivation, but the clinical applications of IP are still limited mainly to respiration rate and apnea detection in hospitalized patients. The emerging applications of IP in respiratory medicine use the measured signal to monitor the pulmonary flow and volume parameters related to airway obstruction during tidal breathing (TB). This places a strict requirement on the linearity between the measured thoracic impedance change ($\Delta Z$) and the lung volume change ($\Delta V$) throughout the complete lung volume range.

In the prior art the impedance pneumography has been applied mostly with deep inspirations, excluding the deep expirations that would reduce the lung volume below the level of normal functional residual capacity (FRC). At low lung volumes the IP signal is highly nonlinear relative to the lung volume. The resting lung volume at which TB occurs, FRC, can change considerably due to many common factors, including supine posture, anatomical differences, mild obesity, and pathological conditions such as chronic obstructive pulmonary disease (COPD) and asthma. Thus, for the emerging IP applications that derive the pulmonary flow parameters, knowledge on the IP signal behaviour on the complete range of lung volume is important. The non-linearity has been a factor reducing the clinical use of IP in flow measurement or in other uses more demanding than respiratory rate monitoring.

The article "An electrical impedance spirometer" by E. S. Goldensohn and L. Zablow, Department of Neurology, College on Physicians and Surgeons, Columbia University, and the Neurological
Institute, Presbyterian Hospital, New York City, 1958; discloses a sensor arrangement of two EKG-type electrodes on the wrists and two similar electrodes placed farther up on each arm.

The article "Impedance pneumograph recording across the arms" by Gershon Weltman and Dnald C. Ukkestad discloses a further study on measuring the respiratory signals across the arms, wherein all sensors are placed on the arms.

SUMMARY

The invention discloses a method for measuring a change in lung volume, comprising measuring a parameter for impedance pneumography by using at least one electrode configured to be in contact with an arm of a human body and at least one electrode configured to be in skin contact with the thorax of a human body. One embodiment of the method uses two electrodes configured to be in contact with one arm of the human body and two electrodes configured to be in skin contact with the thorax of the human body on the side opposite to the arm. One embodiment of the method uses two electrodes configured to be in contact with opposite arms of the human body and two electrodes configured to be in skin contact with the thorax on opposite sides of the human body. The skin contact with the thorax is in one embodiment of the present invention the lateral thorax, on the side of the human body. In one embodiment the skin contact area with the thorax is the midaxillary line of the human body.

In one embodiment of the invention the skin contact between the arm and the torso is prevented by an insulation material configured to be positioned between the arm and the torso. The insulation material is made from a material known from its ability to insulate the electric current such as rubber or plastic. The material may be a hard object, such as a sheet of plastic positioned between the arm and the body, or it may have been formed to a shape to improve comfort. The insulation material may also be soft material; in one example the insulation material is configured to be a sleeve preventing the skin contact. The insulation material may also be configured to be a shirt or a vest preventing the skin contact.

Another aspect of the invention presents a sensor arrangement for measuring a change in lung volume, comprising at least one electrode configured to be in contact with the arm of a human body and at least one electrode configured to be in skin contact with the thorax of a human body and transmitting measurement data to an apparatus for impedance pneumography. Said apparatus is for example purposed to measure a change in the lung volume or it may be used in any other measurement method applying impedance pneumography. According to an embodiment two electrodes are configured to be in contact with one arm of the human body and two electrodes are configured to be in skin contact with the thorax of the human body on the side opposite to the arm. According to an embodiment two electrodes are configured to be in contact with opposite arms of the human body and two electrodes are configured to be in skin contact with the thorax on opposite sides of the human body.

According to one embodiment the sensor is configured to be part of an insulation material preventing the skin contact between the arm and the torso. The insulation material may be configured to be a sleeve preventing the skin contact. The sleeve may be a separate sleeve or part of a shirt or any similar garment. The electrode may also be a fabric electrode configured to be inside the sleeve.

The invention also discloses an apparatus for measuring a change in lung volume by impedance pneumography, characterized by at least one processor and at least one memory including computer program code, the at least one memory and the computer program code arranged to, with the at least one processor, cause the apparatus at least to perform: receiving information from a sensor comprising at least one electrode for impedance pneumography configured to be in contact with the arm of a human body and at least one electrode configured to be in skin contact with the thorax of a human body.

Another aspect of the invention presents a computer program product comprising a computer-readable medium bearing computer program code embodied therein for use with a computer, the computer program code comprising code for receiving information from a sensor comprising an electrode for impedance pneumography configured to be in contact with the arm of a human body.

The present invention provides an improved linearity $\Delta Z/\Delta V$ ratio over the complete lung volume range. The measurement is improved especially with low lung volumes, thus enabling detection of phenomena occurring in that range. The invention also improves the applicability of impedance pneumography in paediatric applications where the comfort of the patient is important.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Reference will now be made in detail to the embodiments of the present invention, examples of which are illustrated in the accompanying drawings.

Figure 1:
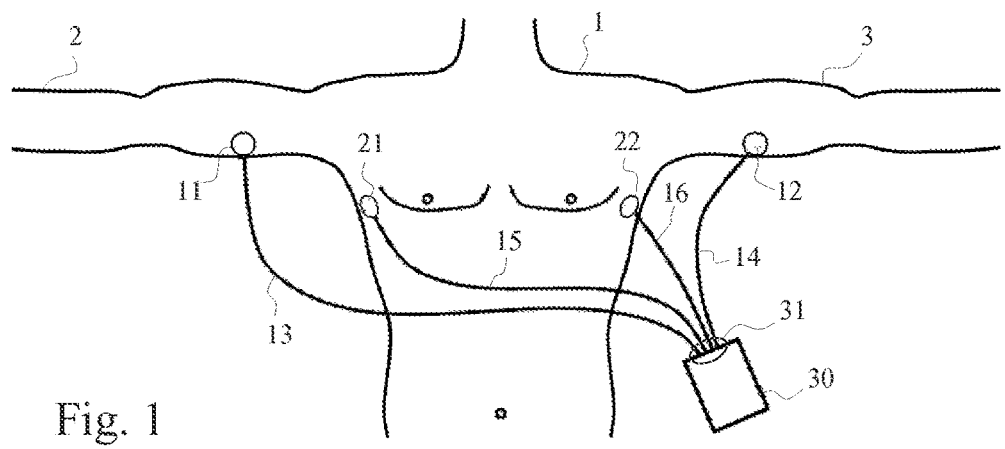
FIG. 1 is a diagram illustrating the elements according to the invention.

FIG. 1 is a block diagram illustrating the elements according to the invention. An apparatus for impedance pneumograhy 30 is connected via a connector interface 31 to the sensor 11 attached to the right arm 2 and the sensor 12 attached to the left arm 3 of a human body 1. Sensors 21, 23 are attached to the side of thorax or to the midaxillary line on both sides of the body 1. The sensor element comprises an electrode and a cable 13, 14, 15, 16 conducting the electrical signal to the connector interface 31. The midaxillary line is defined as a coronal line on the torso between the anterior axillary line and the posterior axillary line. The sensor placement may vary few centimetres from the midaxillary line.

Sensors 11, 12, 21, 22, cables, 13, 14, 15, 16, the interface 31 and the apparatus 30 are components of an impedance pneumography measurement system. The sensors 11, 12, 21, 22 may comprise a text, colour or other indication that helps the person using the impedance pneumography system to connect the sensor to a correct position on the body 1. Sleeves 41, 41 may comprise an indication separating the left arm 2 and the right arm 3. Also the sizing or the form of the sleeve 41, 42 may prevent the user from installing the sensor 11, 12 to a wrong position.

In one embodiment of the invention the interface 31 configured to the apparatus 30 is arranged to comprise indication of a correct installation procedure, such as colour coding or text.

The apparatus 30 may also comprise a display for informing the user about the procedure. The software implemented in the apparatus 30 may also comprise code for providing assistive information to the user, confirming the correct installation procedure or informing about any errors during the installation or operation. One example of an error situation is the measurement data being out of the predefined range.

In one embodiment the computer program code comprises means for detecting the correct sensor 11, 12, 21, 22 being installed into the correct interface 31. The sensor may be configured to send information about the purpose or position in the interface 31 or the interface may have means for detecting the inserted sensor cable 13, 14, 15, 16.

The apparatus 30 may comprise an interface to transmit the impedance pneumography information to another device, such as a computer or another medical device. In one embodiment the apparatus 30 is arranged to convert changes in thoracic impedance resulting from respiration into a high level respiration signal that can be used with other applications. The apparatus 30 may also be integrated into another medical device.

Figure 2:
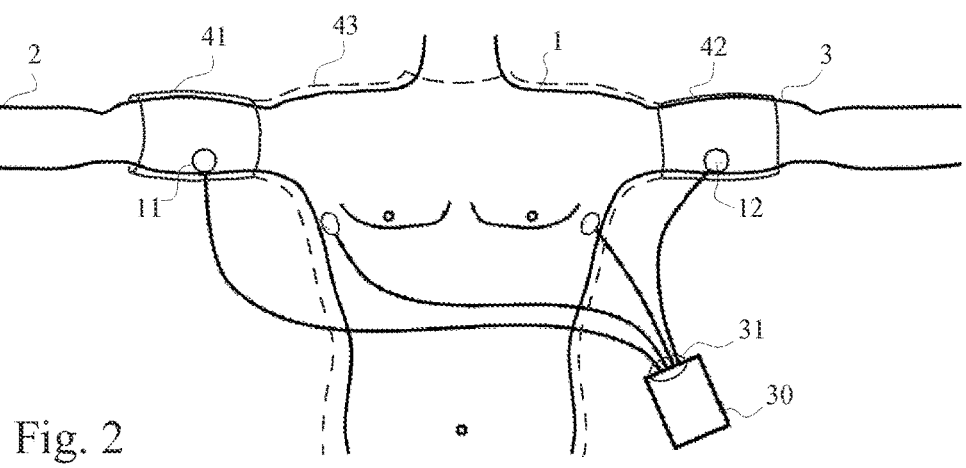
FIG. 2 illustrates the sensor arrangement with a sleeve or a shirt.

FIG. 2 illustrates one embodiment of the invention where sensors 11, 12 are arranged to be part of a sleeve 41, 42. The sleeve 41, 42 is made from electrically resistive material that prevents the direct skin contact between the arm 2, 3 and the torso. This prevents the electrical current from passing through the skin and thus contributing to false values. The bioimpedance values are measured through the high-axillary line or from the preferred path of the upper portion of lungs. The sleeve may also be part of a shirt or jacket 43 arranged to be used with the impedance pneumography system. The sleeve may also be in the form of an armband. In one embodiment the thickness of the armband keeps the arm at a distance from the body. The sleeve may also comprise the electrode configured as a fabric electrode made of suitable material such as silver or platinum.

Figure 3:
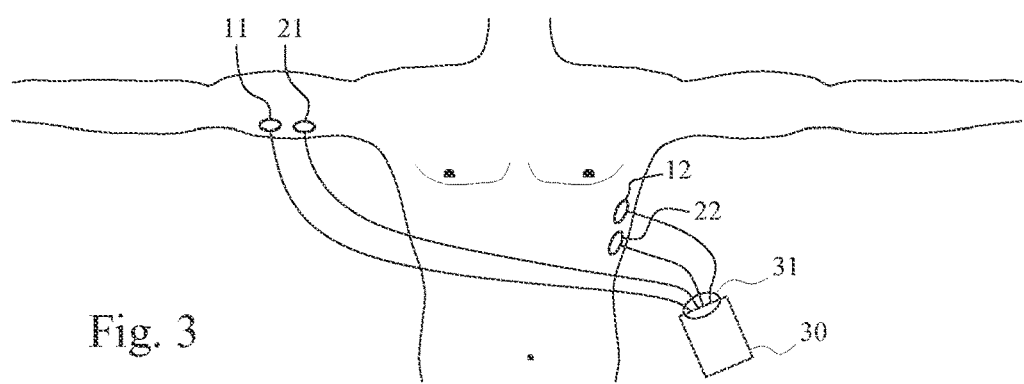
FIG. 3 illustrates one embodiment of the sensor arrangement.

Sensors 11, 12, 21, 22 may be arranged in different configurations. In a tetrapolar bioimpedance measurement four electrodes are used; two for feeding an alternating current of a constant amplitude and two for sensing the voltage. Also a constant voltage may be used while the current is measured. The electrode is measuring for example the voltage differential measured from both arms or the electrodes may be feeding the current to enable measuring of the impedance. The pair of electrodes purposed for the same parameter is always positioned to a distance from each other. For example electrodes feeding the current may be positioned to different arms. Alternatively one may be positioned to the arm and the other to the side of the thorax on the opposite side of the body, as illustrated in FIG. 3. Feeding the current and measuring the voltage may also be combined into a single sensor as a pair of electrodes.

In the impedance pneumography a small high frequency current is passed through a pair of skin electrodes and another pair of electrodes is used to record the generated voltage that is proportional to the impedance (Z), which again is proportional to the lung volume (V). The cardiogenic oscillations can be removed by a filtering technique described in the Finnish patent application FI20115110, which is incorporated by reference into this document.

Placing the electrodes 11, 12 on the arms 2, improves significantly the linearity of the measurement results on a $\Delta Z/\Delta V$ scale, especially at low lung volumes. One exemplary placement of the electrodes is between biceps and triceps brachii muscles. This placement of the electrodes on the arms can be described as placement on the supra-axillary line. Preventing the skin contact between the arms and the sides improves the measurement as the skin contact is not contributing to the bioimpedance value.

The improved linearity may result from the technical features and physiological features such as the motion and shape change of the thorax and thoracic organs, particularly the diaphragm and the liver, and small airway closing and alveolar collapse. After a deep exhale, and generally in lowered FRC, the diaphragm and liver reside more cephalad (headward) and, thus, are closer to the sensitivity field of the recording electrodes. This could be attributed to the finding that the $\Delta Z/\Delta V$ nonlinearity occurs in deep exhales only in the infra-axillary electrode locations. Small airway closure and possibly alveolar collapse occur even in healthy young subjects when the lung volume is lowered below the FRC level. As the lung volume decreases, the smaller, intraparenchumal airways decrease in calibre until they close at low lung volume. During exhalation in an upright posture, this closure occurs predominantly and earlier in the lower part of the lung. As airway closure and alveolar collapse are known to affect the electrical impedance of the lung, this could partially explain why the infra-axillary configurations exhibit the presented $\Delta Z/\Delta V$ nonlinearity.

Figure 4:
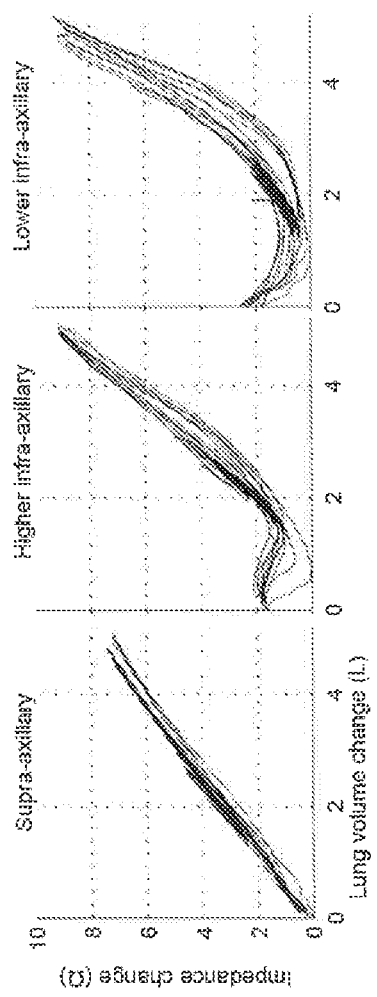
FIG. 4 illustrates examples of the improved $\Delta Z/\Delta V$ non-linearity.

Examples of the improved $\Delta Z/\Delta V$ nonlinearity are illustrated in FIG. 4. The impedance versus lung volume has been measured using the three different sensor placements or electrode configurations referred to as supra-axillary, high infra-axillary and low infra-axillary. The plotted signals include the complete measurement sequence with six vital capacity manoeuvres (VCM) and multiple tidal breaths. The effect is clearly visible especially in low lung volumes.

Figure 5:
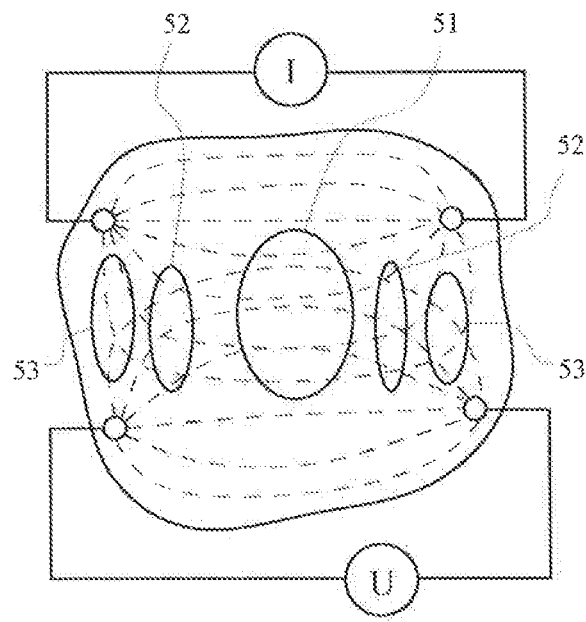
FIG. 5 illustrates a generic example of a bioimpedance measurement arrangement and the lead field theory.

The effect of the present invention may also be explained using the lead field theory. FIG. 5 illustrates a generic example of a bioimpedance measurement arrangement. The lead field theory is applicable to bioimpedance measurements. In a conventional four-terminal (tetrapolar) impedance measurement two terminals act as the current source and sink and the other two as differential voltage pickup terminals. The lead field lines are illustrated in FIG. 5 as dotted lines. As explained in the Master of Science thesis, Bioimpedance in a wireless wearable device; Ville-Pekka Seppä 2007, Tampere University of Technology; the current and the voltage lead fields can be treated as a matrix dot product, being a commutative mathematical operation. The sensitivity field of the electrode configuration is formed by the dot product of the two lead fields. In theory, the voltage sensing and current feeding electrodes can be interchanged without affecting the measurement result. The absolute value of the sensitivity field resulting from the dot product varies in magnitude from point to point in a conductor, but the sign of the value can also change. When the angle of the lead fields is equal to 90°; area 52; the sensitivity value is zero. When the 90° angle is exceeded; area 53; the value turns negative. The measurement value is positively affected when the sensitivity lead lines are parallel; area 51. Therefore the components affecting the overall result are in the area where the two lead fields overlap.

Figure 6:
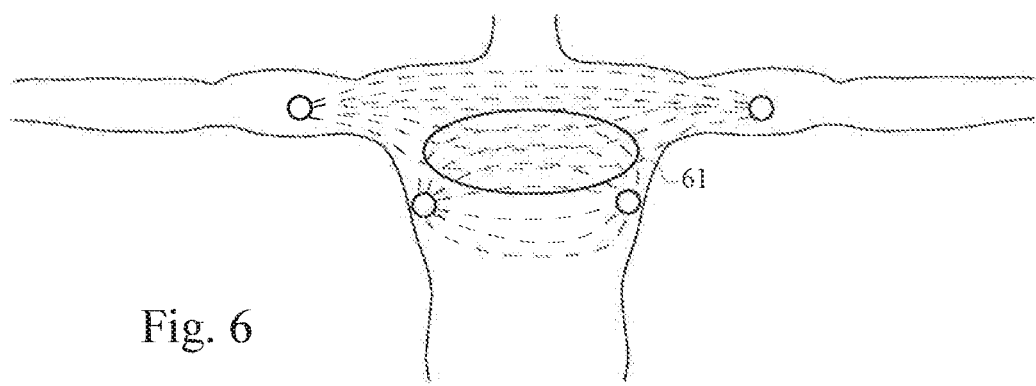
FIG. 6 illustrates the lead field effect according to the invention in a simplified form.

FIG. 6 illustrates the lead field effect in a simplified form. According to the sensor placement according to the present invention, lead fields overlap in the area 61. The majority of the parallel lines occur in the same area as the lungs or the upper portion of the lungs. The resulting effect is that the variable component of the derived signal is obtained mostly from the most important area.

Figure 7A:
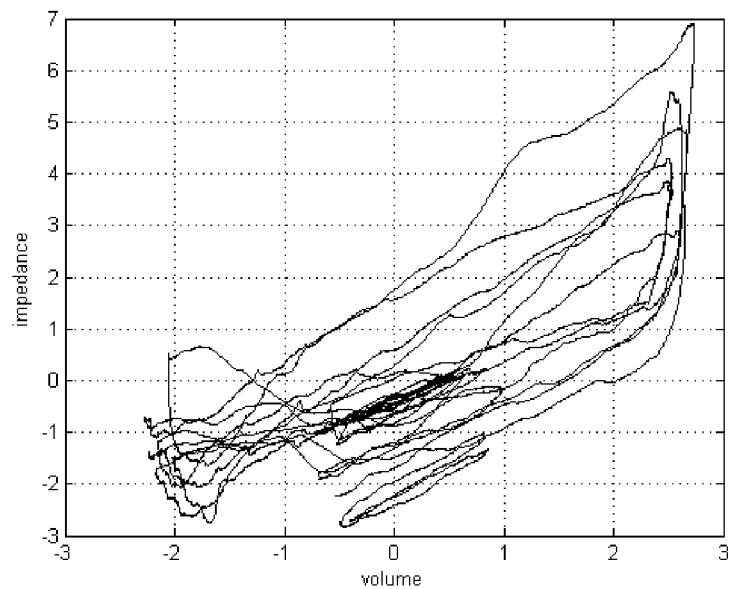
FIG. 7a illustrates the measurement where all sensors are placed in the arms.
Figure 7B:
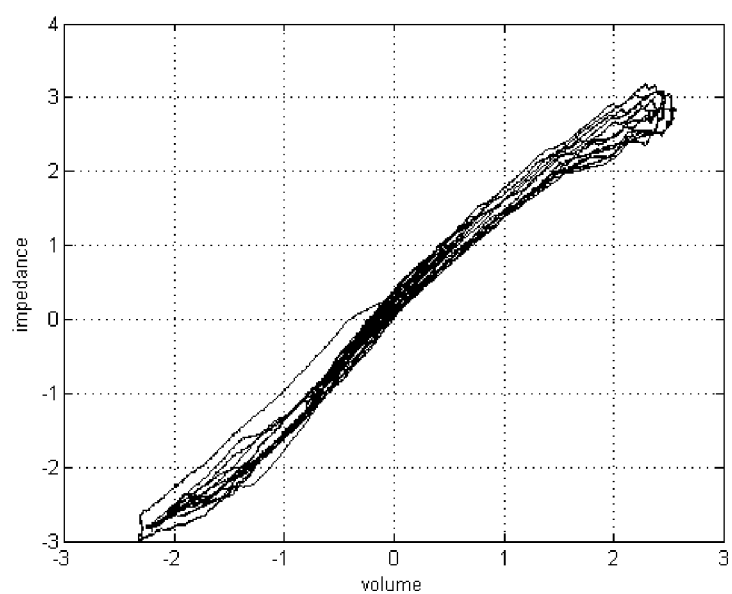
FIG. 7b illustrates the measurement with the sensor placement according to an embodiment of the present invention.

The prior art knows solutions in which all four sensors measuring both the voltage and the current are placed on the arms. However, this arrangement does not provide optimal solution as the nonlinearity is still present. The improvement is illustrated in FIGS. 7a and 7b, wherein the same test subject uses different sensor arrangements. FIG. 7a illustrates the measurement according to the prior art, where all sensors are placed in the arms. The non-linearity is evident, as the measurement curves representing several breathing cycles are distributed to wide area. FIG. 7b illustrates the measurement with the sensor placement according to an embodiment of the present invention. The measurement curves create a uniform pattern with reasonably linear results.

The present invention enables more sophisticated clinical applications of impedance pneumography, particularly in paediatric applications where the comfort and non-invasiveness of the method contribute largely to the behaviour of the patient. As the sensor placement is simple, also the apparatus can be kept simple and portable. One example of the present invention is a respiration monitoring device which collects data in a convenient environment such as the patient's home. Parents may apply the impedance pneumography system according to the invention with their children. The collected data may be stored to the memory of the apparatus or it may be transmitted to another location by means known in the prior art. The data may comprise the respiratory rate, lung volumes as a function of time or in different environments such as during the sleep.

Embodiments of the present invention may be implemented in software, hardware, application logic or a combination of software, hardware and application logic. In an example embodiment, the application logic, software or instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer. A computer-readable medium may comprise a computer-readable storage medium that may be any media or means that can contain or store the instructions for use by or in connection with an instruction execution system, apparatus, or device, such as a computer. The exemplary embodiments can store information relating to various processes described herein. This information can be stored in one or more memories, such as a hard disk, optical disk, magneto-optical disk, RAM, and the like. One or more databases can store the information used to implement the exemplary embodiments of the present inventions. The databases can be organized using data structures (e.g., records, tables, arrays, fields, graphs, trees, lists, and the like) included in one or more memories or storage devices listed herein. The processes described with respect to the exemplary embodiments can include appropriate data structures for storing data collected and/or generated by the processes of the devices and subsystems of the exemplary embodiments in one or more databases.

All or a portion of the exemplary embodiments can be conveniently implemented using one or more general purpose processors, microprocessors, digital signal processors, micro-controllers, and the like, programmed according to the teachings of the exemplary embodiments of the present inventions, as will be appreciated by those skilled in the computer and/or software art(s). Appropriate software can be readily prepared by programmers of ordinary skill based on the teachings of the exemplary embodiments, as will be appreciated by those skilled in the software art. In addition, the exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware and/or software.

If desired, the different functions discussed herein may be performed in a different order and/or concurrently with each other.

Furthermore, if desired, one or more of the above-described functions may be optional or may be combined. Although various aspects of the invention are set out in the independent claims, other aspects of the invention comprise other combinations of features from the described embodiments and/or the dependent claims with the features of the independent claims, and not solely the combinations explicitly set out in the claims.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for measuring a change in lung volume, comprising:
    placing a first pair of electrodes in contact with opposite arms of a human body;
    placing a second pair of electrodes in skin contact with the midaxillary line on opposite sides of the human body;
    measuring a parameter for impedance pneumography by tetrapolar impedance measurement, comprises:
    feeding a current to the first pair of electrodes in contact with the opposite arms of the human body and measuring a voltage by the second pair of electrodes in skin contact with the midaxillary line on opposite sides of the human body, or
    feeding a current to the second pair of electrodes in skin contact with the midaxillary line on opposite sides of the human body and measuring a voltage by the first pair of electrodes in contact with the opposite arms of the human body.

2. The method according to claim 1, comprising preventing skin contact between the arms and a torso by an insulation material positioned between the arms and the torso, causing to prevent the current from passing through the skin contact.

3. The method according to claim 2, wherein the insulation material is a sleeve.

4. The method according to claim 2, wherein the insulation material is a shirt or a vest.

\* \* \* \* \*